US012582373B2

(12) United States Patent
Siversson

(10) Patent No.: US 12,582,373 B2
(45) Date of Patent: *Mar. 24, 2026

(54) GENERATING SYNTHETIC ELECTRON DENSITY IMAGES FROM MAGNETIC RESONANCE IMAGES

(71) Applicant: SPECTRONIC AB, Helsingborg (SE)

(72) Inventor: Carl Siversson, Råå (SE)

(73) Assignee: SPECTRONIC AB, Helsingborg (SE)

( * ) Notice: Subject to any disclaimer, the term of this patent is extended or adjusted under 35 U.S.C. 154(b) by 0 days.

This patent is subject to a terminal disclaimer.

(21) Appl. No.: 18/618,872

(22) Filed: Mar. 27, 2024

(65) Prior Publication Data

US 2024/0298990 A1    Sep. 12, 2024

Related U.S. Application Data

(63) Continuation of application No. 17/605,209, filed as application No. PCT/SE2020/050415 on Apr. 24, 2020, now Pat. No. 11,969,283.

(30) Foreign Application Priority Data

Apr. 26, 2019    (SE) .................................... 1930141-5

(51) Int. Cl.
*A61B 6/00*        (2024.01)
*A61B 5/055*       (2006.01)
(Continued)

(52) U.S. Cl.
CPC ............ *A61B 6/5235* (2013.01); *A61B 5/055* (2013.01); *A61B 6/032* (2013.01); *A61B 6/5205* (2013.01); *A61N 5/1039* (2013.01); *G06N 20/00* (2019.01)

(58) Field of Classification Search
CPC ....... A61B 6/5235; A61B 5/055; A61B 6/032; A61B 6/5205; A61B 6/5229;
(Continued)

(56) References Cited

U.S. PATENT DOCUMENTS 10,540,798 B1 *  1/2020  Walters .................. G06N 20/00
2017/0072222 A1   3/2017  Siversson
(Continued)

FOREIGN PATENT DOCUMENTS

AU        2016338923 A1    4/2018
EP          3373245 A2    9/2018
(Continued)

OTHER PUBLICATIONS

International Search Report and Written Opinion from corresponding International Application No. PCT/SE2020/050415, Jun. 23, 2020, 13 pages.
(Continued)

*Primary Examiner* — Andrew M Moyer
*Assistant Examiner* — Ahmed A Nasher
(74) *Attorney, Agent, or Firm* — Tucker Ellis LLP

(57)                ABSTRACT

A conversion device is operable to perform a learning-based method of generating a synthetic electron density image (sCT) of an anatomical portion based on one or more magnetic resonance (MR) images. The method is processing-efficient and capable of producing highly accurate sCT images irrespective of misalignment in the underlying training set. The conversion device receives and installs a machine-learning model trained to predict coefficients of an image transfer function. The conversion device then receives a current set of MR images of the anatomical portion, computes current coefficients of the image transfer function by operating the machine-learning model on the current set of MR images, and computes a current sCT
(Continued)

image of the anatomical portion by operating the current coefficients, in accordance with the image transfer function, on the current set of MR images.

23 Claims, 7 Drawing Sheets

(51) Int. Cl.
 *A61B 6/03* (2006.01)
 *A61N 5/10* (2006.01)
 *G06N 20/00* (2019.01)

(58) Field of Classification Search
 CPC .... A61B 6/5247; A61N 5/1039; G06N 20/00;
 G06T 2207/10088; G06T 2207/20081;
 G06T 2207/20084; G06T 2207/30004;
 G06T 11/001; G01R 33/4812; G01R
 33/5608; G16H 50/20; G16H 30/40
 See application file for complete search history.

(56) References Cited

U.S. PATENT DOCUMENTS

| | | | |
|---|---|---|---|
| 2017/0337682 A1 | 11/2017 | Liao | |
| 2018/0228460 A1 | 8/2018 | Singh | |
| 2019/0042885 A1 | 2/2019 | Han | |
| 2019/0311228 A1* | 10/2019 | Zhao | G06T 7/0014 |
| 2019/0333219 A1* | 10/2019 | Xu | G06N 3/045 |
| 2019/0362522 A1* | 11/2019 | Han | A61B 5/7267 |
| 2021/0016109 A1 | 1/2021 | Sjolund | |
| 2024/0118359 A1* | 4/2024 | Schlemper | G06T 11/008 |

FOREIGN PATENT DOCUMENTS

| | | | |
|---|---|---|---|
| WO | 2018015414 A1 | 1/2018 | |
| WO | 2018048507 A1 | 3/2018 | |
| WO | 2018048575 A1 | 3/2018 | |

OTHER PUBLICATIONS

Andreasen et al., "Computed Tomography synthesis from Magnetic Resonance images in the pelvis using multiple Random Forests and Auto-Context features," SPIE Medical Imaging, vol. 9784, dated 2016, 9 pages.

Tonghe et al., "MRI-based treatment planning for brain stereotactic radiodurgery: Dosimetric validation of learning-based pseudo-CT generation method," Medical Dosimetry, nr. 3, vol. 44; dated 2018; pp. 199-204.

Arabi et al., "Comparision of synthetic CT generation algorithms for MRI-only radiation planning in the pelvic region," IEEE Nuclear Science Symposium, dated 2018, 3 pages.

Shafai-Erfandi et al., "Dose evaluation of MRI-based synthetic CT generated using a machine Learning method for prostate cancer radiotherapy," Medical Dosimetry, vol. 44, nr. 4, dated 2019, pp. 64-70.

Han, "MR-based synthetic CT generation using a deep convolutional neural network method," Med. Phys., 44(4), dated 2017, pp. 1408-1419.

Hyunh et al., "Estimating CT Image from MRI Data Using Structured Random Forest and Auto-context Model," IEEE Trans Med Imaging 35(1), Jan. 2016, pp. 174-183.

Korhonen et al., "A dual model HU conversion from MRI intensity values within and outside a bone segment for MRI-based radiotherapy treatment planning of prostate cancer," Med. Phys. 41, 011704 dated 2014, 13 pages.

Li et al., "Deep Learning Based Imaging Data Completion for Improved Brain Disease Diagnosis", Med. Image Comput. Assist Interv. 17(0 3), dated 2014, pp. 305-312.

Su et al., "Generation of brain pseudo-CTs using an undersampled, single-acquisition UTE-mDixon pulse sequence and unsupervised clustering," Med. Phys. 42 (8), Aug. 2015, 13 pages.

Office Action from corresponding Japanese Application No. 2021-563284 mailed on Mar. 19, 2024, 6 pages with translation.

\* cited by examiner

30

CT

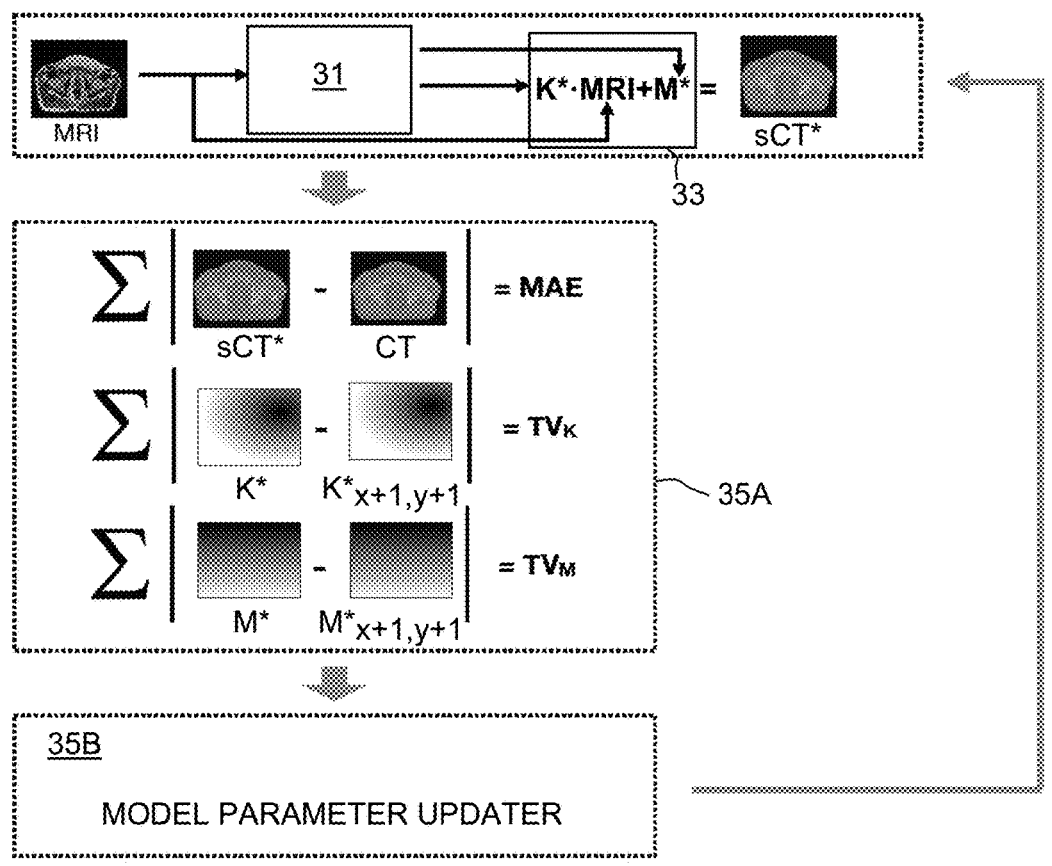
FIG. 8B
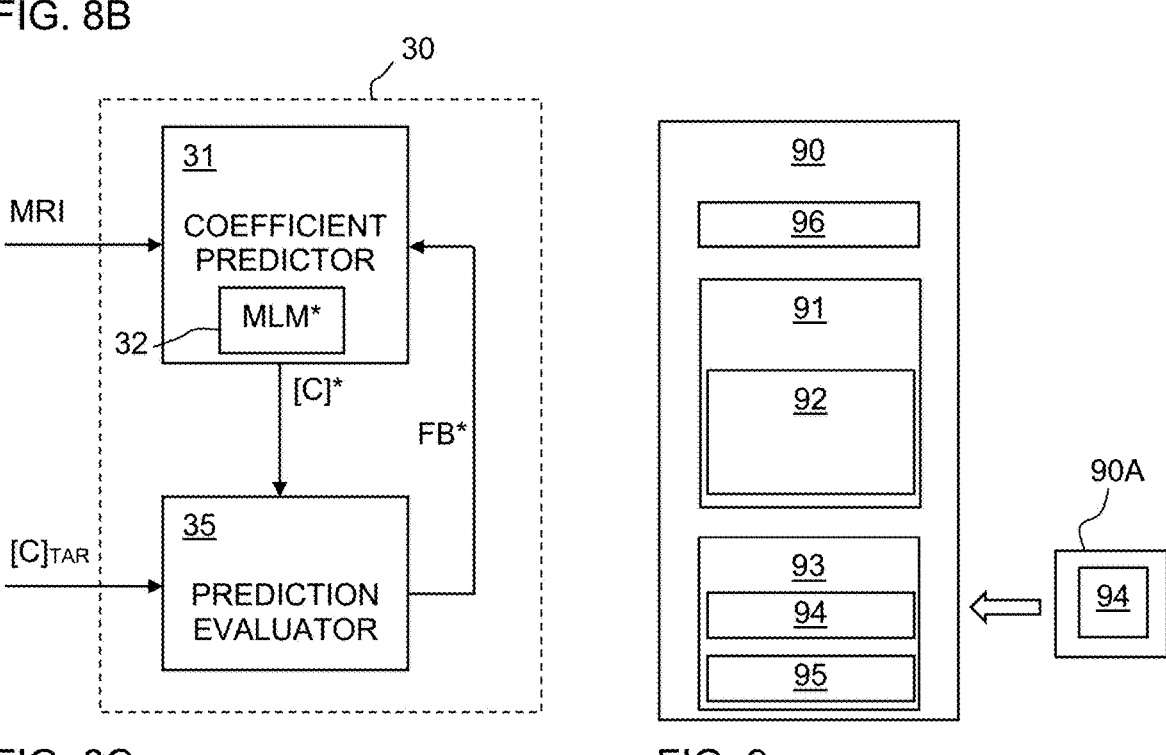
FIG. 8C                                        FIG. 9

GENERATING SYNTHETIC ELECTRON DENSITY IMAGES FROM MAGNETIC RESONANCE IMAGES

RELATED APPLICATION DATA

This application is a continuation of U.S. patent application Ser. No. 17/605,209, filed Oct. 20, 2021, which is a National Phase Entry of International Patent Application No. PCT/SE2020/050415, filed Apr. 24, 2020, and claims priority to Swedish Patent Application No. 1930141-5, filed Apr. 26, 2019, the disclosures of which are each incorporated herein by reference in their entireties.

TECHNICAL FIELD

The present invention relates generally to the field of medical imaging and, more particularly, to a technique for generating synthetic electron density images from magnetic resonance images, e.g. for use in planning of external radiotherapy treatment.

BACKGROUND

In traditional planning of radiotherapy treatment, e.g. of cancer, a computed tomography (CT) image is acquired of an anatomical portion of the patient and used as basis for optimizing the treatment plan. CT or "CT scan" refers to a medical imaging technique that measures attenuation of radiation, typically x-rays, when passing through an object from different angles, and that reconstructs 2D or 3D images ("tomograms") of the object based on the measured attenuation. The values in the resulting CT image thereby represents how the object responds to the radiation and may be directly converted to electron densities, e.g. so-called Hounsfield units (HU), and used for radiation dose calculation.

When creating the treatment plan, it is also necessary to delineate the target area for the radiotherapy, e.g. one or more tumors with some added margin. Often, it is also necessary to delineate so-called organs at risk (OARs), which are sensitive and vital organs that should be exposed to a minimum of radiation. A drawback of CT is that soft tissue structures are difficult to separate in CT images. Delineating using only CT images therefore entails guesswork and large margins. To alleviate this problem, modern radiotherapy often also involves an additional MRI scan. MRI (Magnetic Resonance Imaging) refers to an imaging technique that uses powerful magnetic fields, magnetic field gradients, and radio waves to generate tomographic 2D or 3D images of organs and structures in the body. MRI is free of ionizing radiation and offers superior soft tissue contrast that allows more accurate target and structure delineation. However, since MR images do not contain electron density information, a combined CT/MRI workflow is conventionally used in radiotherapy planning. The combined CT/MRI workflow is expensive and time consuming and also adds additional discomfort to the patient. Further, CT itself adds a significant radiation dose to the patient, which limits its repeated use on a patient.

To overcome these drawbacks, MRI-only workflows have been proposed, in which MRI data is processed algorithmically to synthetically generate electron density images, known as "pseudo CT", "substitute CT" or "synthetic CT" (sCT), thereby obviating the need for CT scans. One major challenge in this context is the lack of correspondence between the respective pixel intensity in an MR image and the associated radiation attenuation property of the tissue. MRI intensities rather correlate with tissue proton density and magnetic relaxation. This leads to ambiguity between tissues in the MR image. For example, bone and air both appear dark in MR images although they have very different radiation attenuation properties.

Known techniques for sCT may be broadly divided into three categories: atlas-based approach, segmentation-based approach, and learning-based approach.

The atlas-based approach uses a database of pre-matched MR and CT images, denoted MR and CT atlases or templates. MR atlases from the database are then registered by deformation with a new incoming MR image, and the same deformation is then applied to CT atlases which are combined to generate an sCT image. Atlas-based approaches are generally quite time consuming.

The segmentation-based approach is exemplified in the article "A dual model HU conversion from MRI intensity values within and outside a bone segment for MRI-based radiotherapy treatment planning of prostate cancer", by Korhonen et al, published in Med. Phys. 41, 011704 (2014). A conversion model for soft tissue and bony tissue, respectively, is determined by comparing, e.g. by regression analysis, bulk intensity values within well-defined regions-of-interest (ROIs) in MR images and standard CT images. A new incoming MR image is then manually segmented and the respective conversion model is applied to the respective segment to transform the MR image into an sCT image. This approach relies on tissue segmentation, which may be difficult to perform automatically on MR images with high accuracy. Further, dividing the anatomy into few tissue types provides a coarse approximation of the actual anatomy.

The learning-based approach involves training and using machine-learning methods for direct conversion from a first to a second medical imaging modality. A technique of training a convolutional neural network (CNN) to convert MR images into sCT images is disclosed in the article "MR-based synthetic CT generation using a deep convolutional neural network method", by Xiao Han, published in Med. Phys., 44(4), pp 1408-1419 (2017). A similar disclosure of direct image-to-image mapping is found in WO2018/048507. In fact, this technique was known in the scientific community well before 2017. For example, a technique of training a convolutional neural network (CNN) to convert MR images into PET images is disclosed in the article "Deep Learning Based Imaging Data Completion for Improved Brain Disease Diagnosis", by Li et al, published in Med Image Comput Comput Assist Interv. 2014; 17(0 3): 305-312. Further, methods of using machine-learning methods to convert MR images into estimated CT images are disclosed in the articles "Estimating CT Image from MRI Data Using Structured Random Forest and Auto-context Model", by Huynh et al, published in IEEE Trans Med Imaging. 2016 January; 35(1): 174-183, and "Generation of brain pseudo-CTs using an undersampled, single-acquisition UTE-mDixon pulse sequence and unsupervised clustering", by Su et al, published in Med. Phys. 42 (8), August 2015.

The learning-based approach generally employs a large training set of matched MR and CT images, by which an artificial neural network (ANN) or the like is trained to generate sCT images based on incoming MR images. In the training, the ANN will fit an unstructured non-linear function to each pixel based on a finite neighborhood (receptive field) around the pixel, based on the entire training set. This means that fine details in the sCT are lost if there are small errors in the matching between MR and CT images in the training set.

3

SUMMARY

It is an objective of the invention to at least partly overcome one or more limitations of the prior art.

A further objective is to provide a technique for generating synthetic electron density images based on MR images of an anatomical portion.

A yet further objective is to provide such a technique capable of being automated.

Another objective is to provide a technique capable of generating the synthetic electron density images with high level of detail and accuracy.

One or more of these objectives, as well as further objectives that may appear from the description below, are at least partly achieved by a computer-implemented methods and a device for generating a synthetic electron density image of an anatomical portion, a machine-learning model, computer-implemented methods of providing a trained machine-learning model, and computer-readable media according to the independent claims, embodiments thereof being defined by the dependent claims.

Still other objectives, as well as features, aspects and technical effects of the present invention will appear from the following detailed description, the attached claims and the drawings.

BRIEF DESCRIPTION OF DRAWINGS

Embodiments of the invention will now be described in more detail with reference to the accompanying schematic drawings.

FIG. 9 is a block diagram of a device that may implement methods of generating sCT images and/or training a machine-learning model in accordance with some embodiments of the present disclosure.

DETAILED DESCRIPTION OF EXAMPLE EMBODIMENTS

Figure 1:
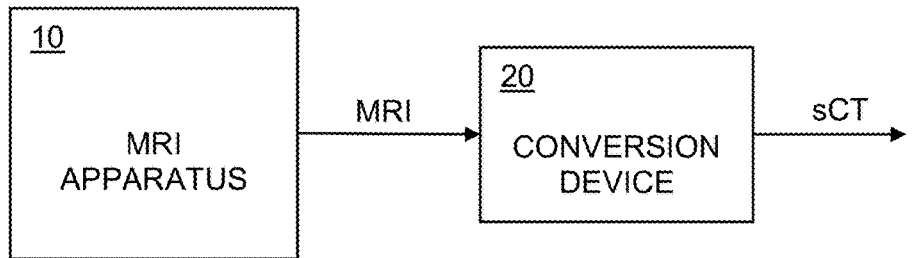
FIG. 1 is a block diagram of an exemplary MRI-only imaging system.

Embodiments of the present invention will now be described more fully hereinafter with reference to the accompanying drawings, in which some, but not all, embodiments of the invention are shown. Indeed, the invention may be embodied in many different forms and should not be construed as limited to the embodiments set forth herein; rather, these embodiments are provided so that this disclosure may satisfy applicable legal requirements. Like numbers refer to like elements throughout.

Also, it will be understood that, where possible, any of the advantages, features, functions, devices, and/or operational aspects of any of the embodiments of the present invention described and/or contemplated herein may be included in any of the other embodiments of the present invention described and/or contemplated herein, and/or vice versa. In addition, where possible, any terms expressed in the singular form herein are meant to also include the plural form and/or vice versa, unless explicitly stated otherwise. As used herein, "at least one" shall mean "one or more" and these phrases are intended to be interchangeable. Accordingly, the terms "a" and/or "an" shall mean "at least one" or "one or more", even though the phrase "one or more" or "at least one" is also used herein. As used herein, except where the context requires otherwise owing to express language or necessary implication, the word "comprise" or variations such as "comprises" or "comprising" is used in an inclusive sense, that is, to specify the presence of the stated features but not to preclude the presence or addition of further features in various embodiments of the invention. As used herein, a "set" of items is intended to imply a provision of one or more items.

It will furthermore be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing the scope of the present invention. As used herein, the term "and/or" includes any and all combinations of one or more of the associated listed items.

As used herein, "synthetic electron density image" refers to any type of image that is computationally generated to contain signal values ("intensity values") directly related to electron density. Such images may represent, replace or supplement electron density images generated by computed tomography (CT) using radiation in any wavelength range, including but not limited to x-ray radiation. In the description to follow, a synthetic electron density image is denoted "sCT image" for brevity.

As used herein, "MR image" refers to any type of image generated by an apparatus configured to detect nuclear magnetic resonance (NMR) signals, e.g. an MR scanner of any configuration. In the drawings, an MR image is designated "MRI".

As used herein, an "image" may be two-dimensional (2D) or three-dimensional (3D). A 3D image corresponds to a stack of spatially adjacent 2D images and is commonly denoted "image stack" in the field of tomographic imaging. Each 2D image corresponds to a cross-sectional slice through the object that is being imaged.

As used herein, a "pixel" is an image element and is associated with a pixel value. In 2D images, the location of a pixel may be defined in a 2D regular grid with a fixed location in relation to the respective 2D image, e.g. by (x,y) values. In 3D images, pixels are also known as "voxels", and the location of the pixel may be defined in a 3D regular grid with a fixed location in relation to the respective 3D image, e.g. by (x,y,z) values. As used herein, a pixel may correspond to the smallest individual element in the image, or a group of such elements.

As used herein, a "matrix" is an array of any dimension. The array comprises elements that may be populated by a respective value. For example, a matrix may have two or three dimensions. The term matrix may also be denoted "tensor" in the context of the present disclosure.

As used herein, a "machine-learning model" refers to any type of predictive model that may be trained to predict numeric values, including but not limited to artificial neural networks (ANN), such as deep learning networks, recurrent neural networks, etc., as well as support vector machines (SVM) and bayesian networks, etc.

In the description to follow, the machine-learning model is designated MLM, where a trained MLM is indicated by subscript T (MLMT) and a non-trained MLM is indicated by an asterisk (MLM*). In this context, the process of operating a trained MLM on new input data to generate a result is commonly denoted "inference".

Embodiments of the present invention relate, in general, to the field of generating synthetic electron density information from one or more MR images. The forming of synthetic electron density information may be particularly useful for MR based radiation treatment planning. However, it should be realized that it may be used in other applications as well. For instance, the synthetic electron density information may be used as attenuation information for a positron emission tomography (PET) camera or a single-photon emission computed tomography (SPECT) camera. The synthetic electron density may also constitute proton stopping power information for use in proton radiotherapy planning.

Embodiments are based on the insight that it would be possible to improve the level of detail and accuracy in the synthetic electron density image compared to existing techniques, by operating an "optimized" image transfer function on the one or more MR images. Embodiments are also based on the insight that a properly trained machine-learning model may provide such an "optimized" image transfer function, which thus may be trained to parameterize an image transfer function for an incoming set of MR images such that the synthetic electron density image is obtained by operating the parameterized image transfer function of the set of MR images.

Thus, in contrast to the conventional learning-based approach, the trained machine-learning model does not directly output the synthetic electron density image but rather parameterizes the image transfer function, which thereby is tailored to yield the synthetic electron density image when operated on the input to the machine-learning model. Further, as will be exemplified further below, the machine-learning model may be trained to parameterize the image transfer function without the need for segmentation of the incoming MR image(s), which increases the versality of the technique and allows the technique to be automated and thus performed without subjective human input.

FIG. 1 schematically depicts an MRI-only imaging system which comprises an MRI apparatus 10 configured to generate one or more MR images of an anatomical portion of a patient (not shown). The MRI apparatus 10, commonly known as a scanner, is well-known in the art and will not be further described. A conversion device 20 is configured to receive and process the MR image(s) to generate and output an sCT image. As exemplified in the Background section, the sCT image may then be analyzed together with the MR image(s) for planning of radiotherapy treatment. Alternatively or additionally, the sCT image may be analyzed for any other purpose in which the sCT image replaces a CT image that would have been obtained by conventional CT equipment.

Figure 2:
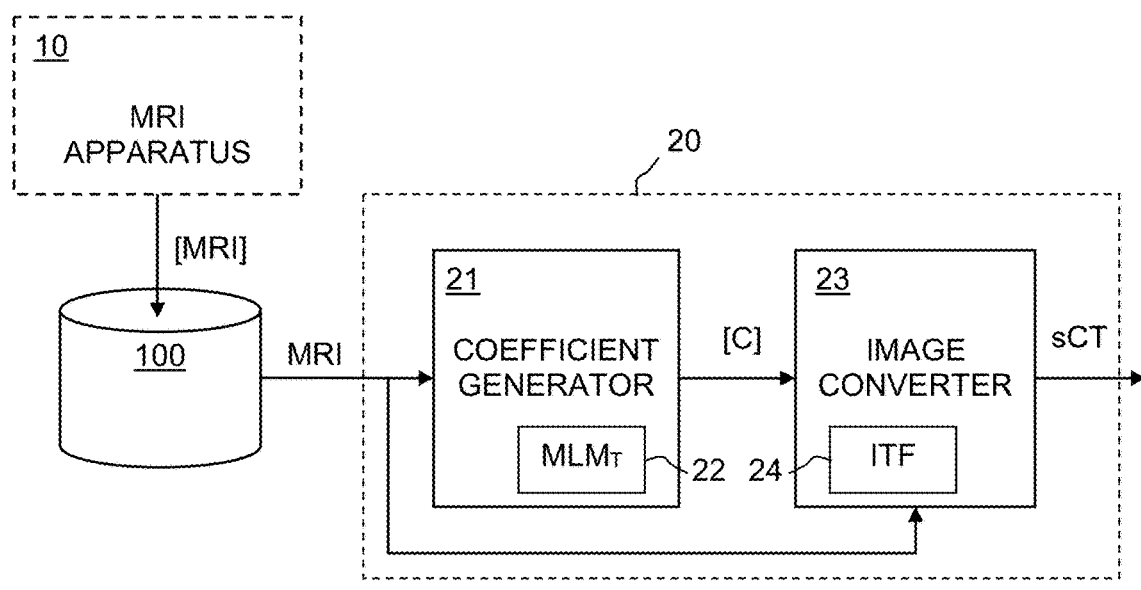
FIG. 2 is a block diagram of an imaging system in accordance with some embodiments of the present disclosure.

FIG. 2 is a more detailed view of an MRI-only imaging system in accordance with an embodiment. In the illustrated example, the conversion device 20 is configured to retrieve MR image(s) from a memory device or storage 100, in which a plurality of MR images, [MRI], generated by the MR apparatus 10 are stored. The conversion device 20 comprises a coefficient generator 21 which operates a trained machine-learning model, MLMT, 22 on incoming MR image(s) to generate and output a current set of coefficients [C] of a predefined image transfer function, ITF. The ITF is a parametric function that takes one or more pixel values in the MR image(s) as input (independent variable) and produces a pixel value (dependent variable) in the sCT image. As used herein, a "coefficient" represents any unknown value that is needed to complete the ITF to enable computation of the dependent variable based on the independent variable(s). In other words, the coefficient(s) are applied to parameterize the ITF. In an example, the ITF is an affine function given by $k \cdot I_p + m$, where $I_p$ is the pixel value in an incoming MR image and k, m are coefficients. An affine ITF has been found to provide a reasonable compromise between computation complexity and accuracy of the resulting sCT image. However, generally, the ITF may be any suitable function, including but not limited to a polynomial function of any degree.

In the following examples, it is assumed that the same ITF is applied for all pixels in the incoming MR image(s), but that the coefficient(s) may vary between pixel locations in the MR image(s). Thus, the above-described affine ITF may be represented by $K \cdot MRI + M$, where K and M are matrices that define coefficients to be applied to individual pixel values in an MR image, MRI. Thus, in this example, the set of coefficients [C] includes the K and M matrices.

It may be noted that the conversion device 20 may operate on more than one MR image to generate the sCT image. In one example, two or more MR images may be generated during one acquisition sequence of the MR apparatus 10 to emphasize different tissues of the patient, e.g. so-called Dixon images which separately emphasize fat and water. Such MR images are known as "multi-channel" MR images in the art. In another example, different acquisition sequences of the MR apparatus 10 may produce MR images with different image contrasts, e.g. so-called T1-weighted and T2-weighted images. Any two or more MR images from one or more acquisition sequences may be jointly processed by the conversion device 20 into the sCT image.

The conversion device 20 further comprises an image converter 23 which is configured to receive [C] from the coefficient generator 21 and to apply [C] to parameterize the ITF 24. The image converter 23 is further configured to receive the current MR image(s), i.e. the same MR image(s) that were processed by the coefficient generator 21, and to apply the currently parameterized ITF on the MR image(s) to generate the current sCT image. Generally, by the parameterized ITF, the image converter 23 may be seen to apply the current coefficients [C] in accordance with the ITF on the current MR image(s).

Figure 3A:
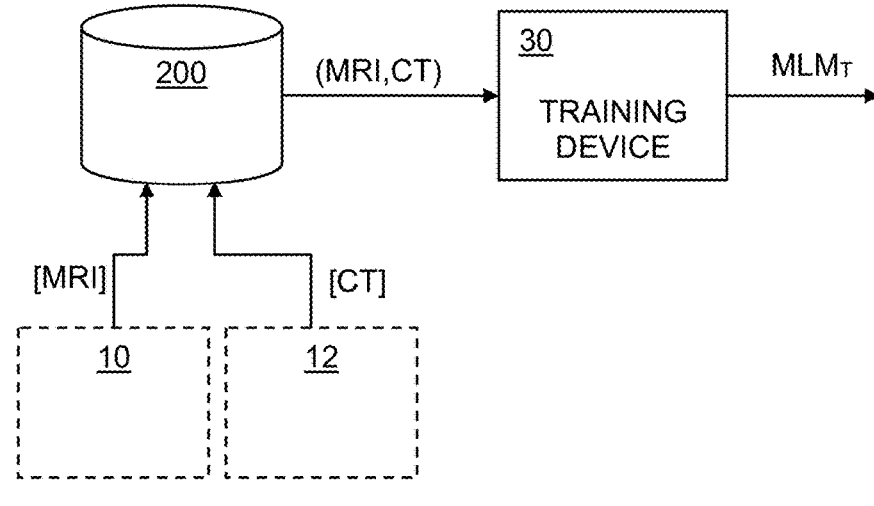
FIG. 3A is a block diagram of a system for training a machine-learning model to be used in the imaging system of FIG. 2.

FIG. 3A illustrates a training system for generating the trained machine-learning model MLMT for use in the conversion device 20 of FIG. 2. The training system comprises a training device 30 which is configured to retrieve matched MR and CT images from a memory device 200 for use in producing the trained machine-learning model, MLMT. As indicated, the memory device 200 stores a plurality of MR images, [MRI], acquired by an MRI apparatus 10, and a corresponding plurality of real CT images, [CT], acquired by a conventional CT apparatus 12. The images [MRI], [CT] form a so-called training set. FIG. 3C exemplifies such a training set 210, which comprises N matched MR and CT images. However, as understood from the foregoing, it is also conceivable that more than one MR image, e.g. multi-channel MR images, is matched to the CT image in the training set and thus used for training the machine-learning model. Further, although the training set 210 is shown to comprise matched 2D images in FIG. 3C, it is equally possible that the training set 210 comprises matched 3D images. In fact, it is currently believed that improved performance, in terms of level of detail and accuracy of the sCT images generated by the conversion device 20 (FIG. 2), is achieved by training the machine-learning model on matched 3D images, since the machine-learning model is thereby trained to also take into account structures in the z direction of the MR and CT images. The improved performance of the conversion device 20, when operating such a trained machine-learning model, is achieved for either 2D or 3D MR images.

The training device 300 may operate on a large number of matched MR and CT images acquired from one or more patients. Typically, the machine-learning model may be trained on tens or even hundreds, or more, of matched 2D or 3D images. The images in the training set may be acquired for a selected anatomical area on the patients, e.g. head, torso, abdomen, limb, etc., and thus the machine-learning model may be trained to operate specifically on MR images acquired from the selected anatomical area.

Figure 3B:
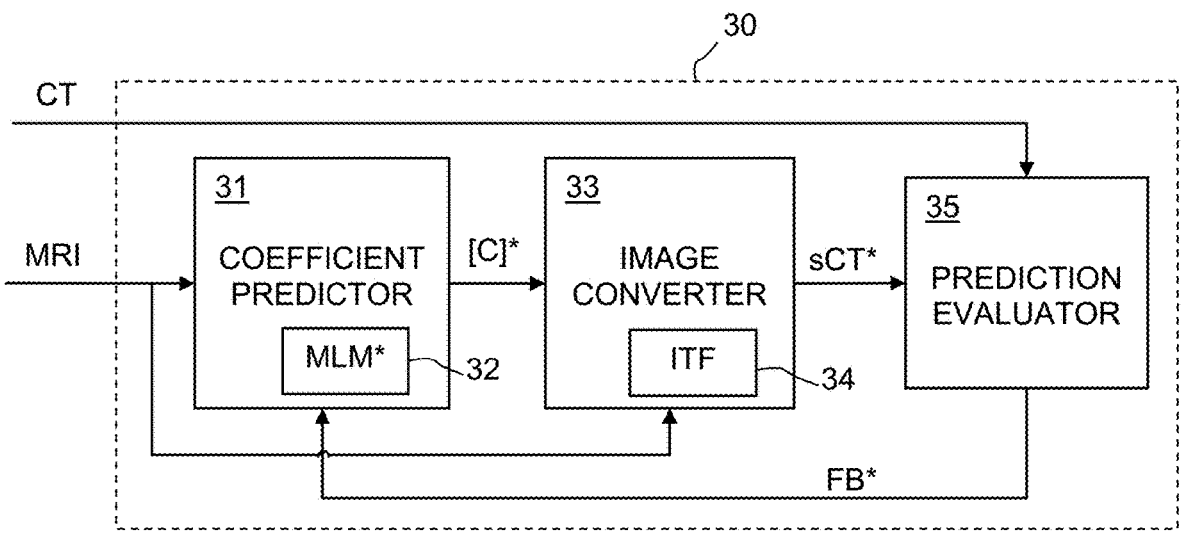
FIG. 3B is a detailed block diagram of a training device in the system of FIG. 3A.
Figure 3C:
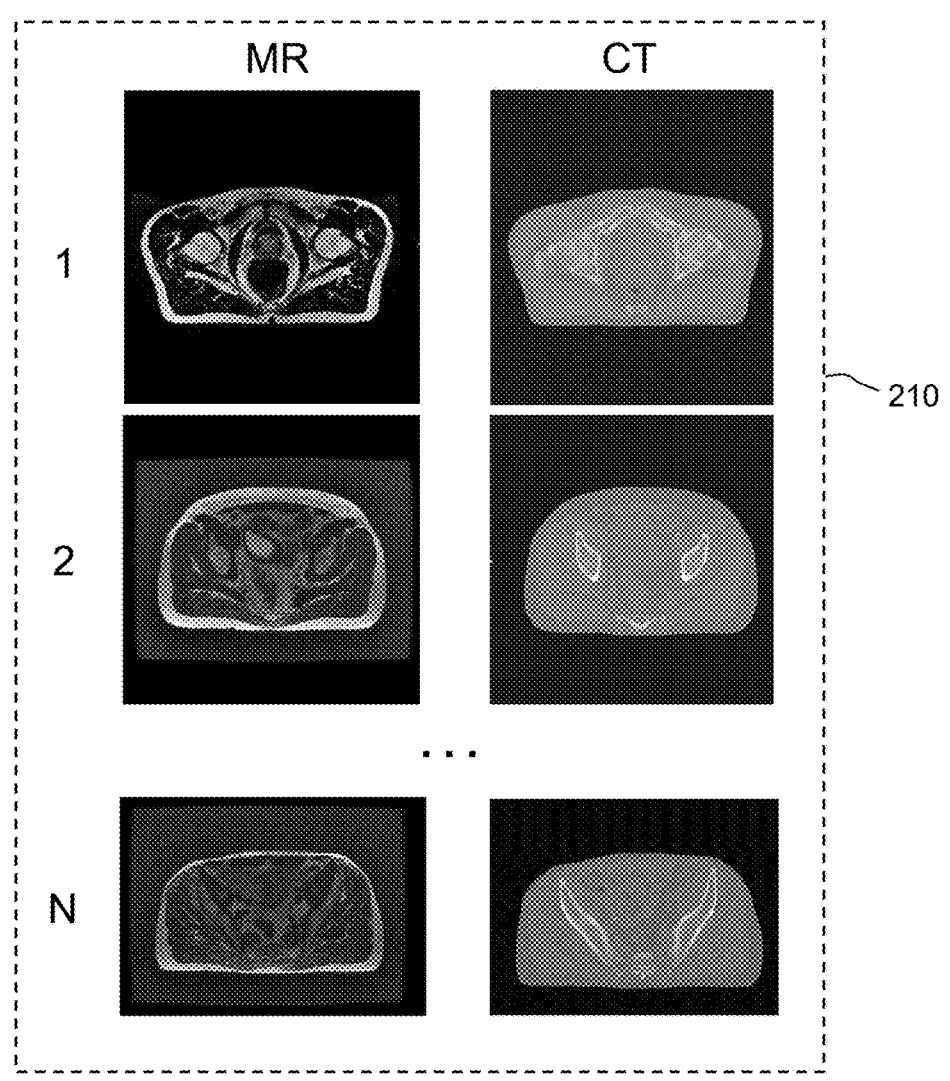
FIG. 3C depicts training data for use in the system of FIG. 3A.

FIG. 3B is a more detailed view of the training device 30 in accordance with an embodiment. In the illustrated example, the training device 30 is configured to retrieve a current data set of matched MR and CT images, e.g. from the memory device 200 (FIG. 3A). The training device 30 comprises a coefficient predictor 31 which comprises the machine-learning model MLM* 32 to be trained. The coefficient predictor 31 corresponds to the coefficient generator 21 but is configured to, in response to feedback data FB* (below), modify model parameters of the MLM* and output a predicted set of coefficients [C] *. The training device 30 further comprises an image converter 33, which corresponds to the image converter 23 and is configured to receive and apply [C]* to parameterize the ITF 34, which is identical to the ITF 24 in the conversion device 20. The image converter 33 is further configured to receive the MR image(s) of the current data set and apply the currently parameterized ITF on the MR image(s) to generate a current predicted sCT image, designated sCT* in FIG. 3B. A prediction evaluator 35 is configured to apply a correction algorithm to generate the feedback data FB*. In one embodiment, the correction algorithm operates to optimize a cost function, which takes the sCT* image and the CT image of the current data set as input. As will be exemplified further below, the cost function may operate on further input data, e.g. [C]* or part thereof.

In the embodiment of FIG. 3B, the training device 30 automatically trains MLM* based on the training set to learn parameters or weights of MLM*. The parameters may be learned iteratively according to an optimality criterion, e.g. defined by the cost function. Specifically, the training device 30 may be seen to train MLM* until a similarity criterion is fulfilled between the CT image, which may be regarded as a reference image, and the sCT* image. The training device 30 may then output the trained machine-learning model MLMT for subsequent installation in the conversion device 20 (FIG. 2).

In one non-limiting example, the machine-learning model is a neural network for deep learning, e.g. a convolutional neural network (CNN). Such a neural network includes a stack of distinct layers that are configured to transform an input into an output. The layers may differ in input size, output size, and the relationship between the input and the output for the layer. Each layer may be connected to one or more upstream and downstream layers in the stack of layers. For deep learning, the convolutional neural network typically has more than one stage of non-linear feature transformation.

Figure 4A:
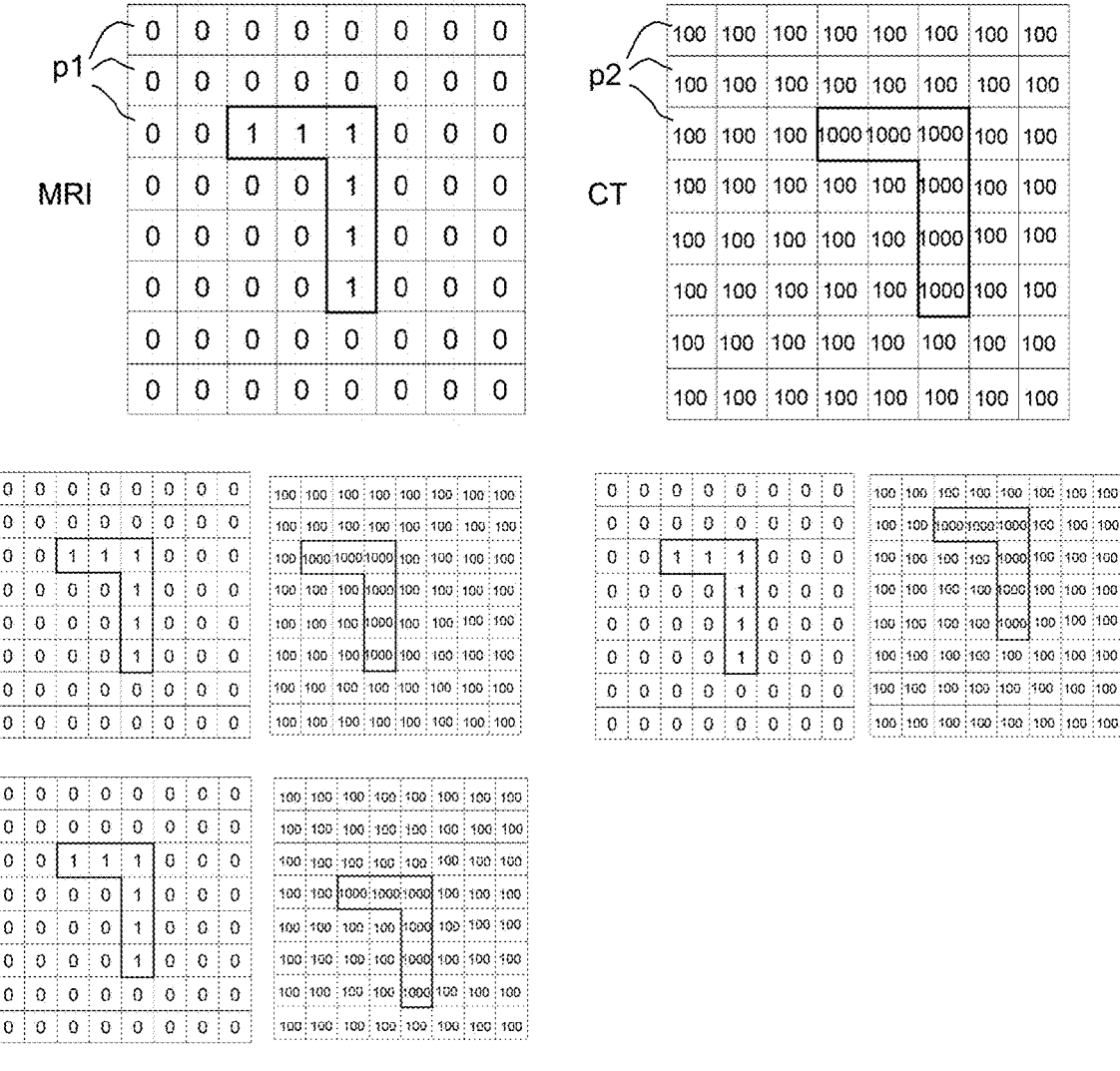
FIGS. 4A-4C are simplified examples of MR and CT images used for training and a resulting sCT image generated by conventional technique (FIG. 4A) and by a method (FIGS. 4B-4C) in accordance with some embodiments of the present disclosure.
Figure 4A:
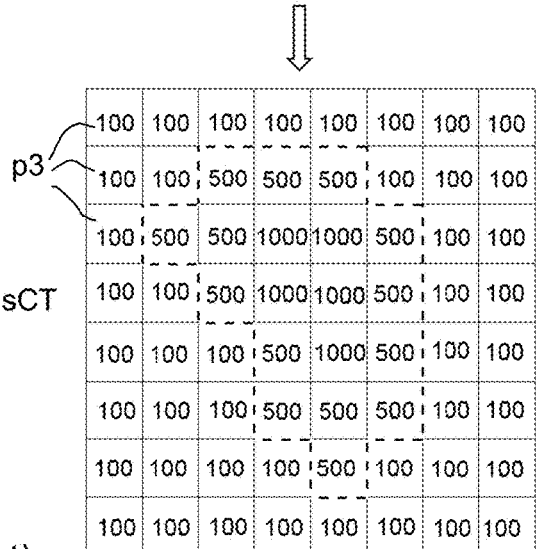
Figure 4B:
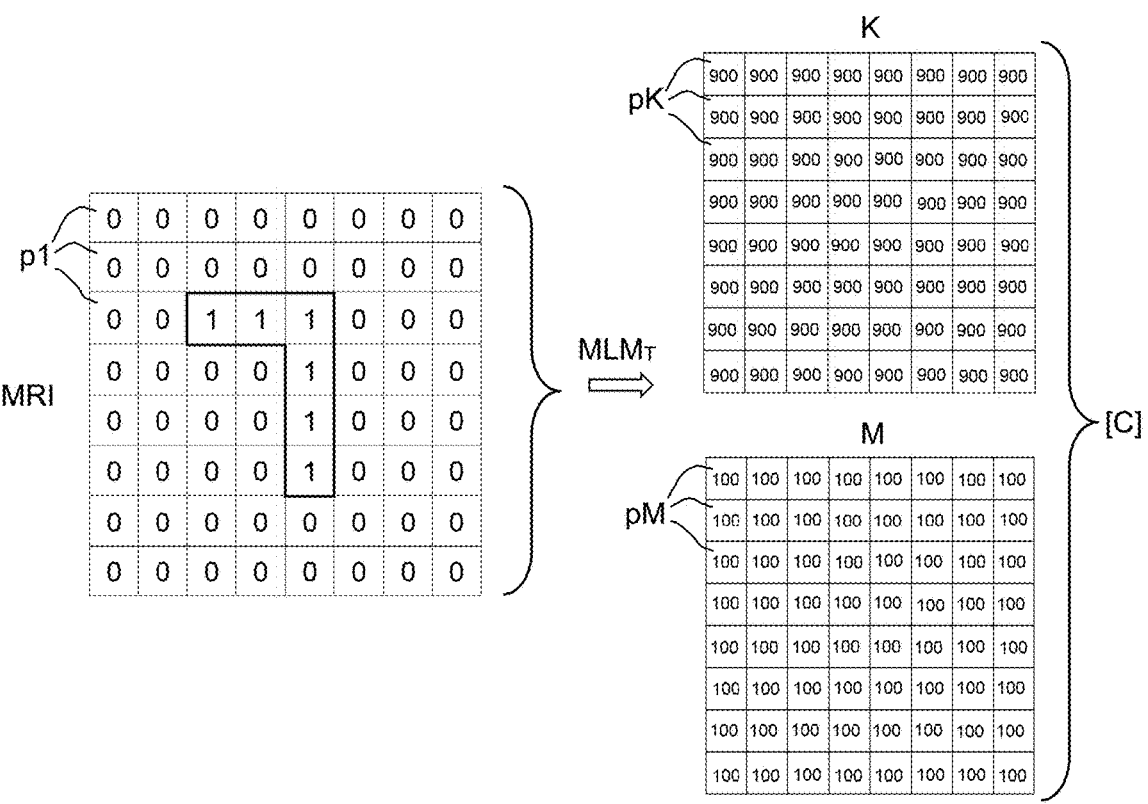
Figure 4C:
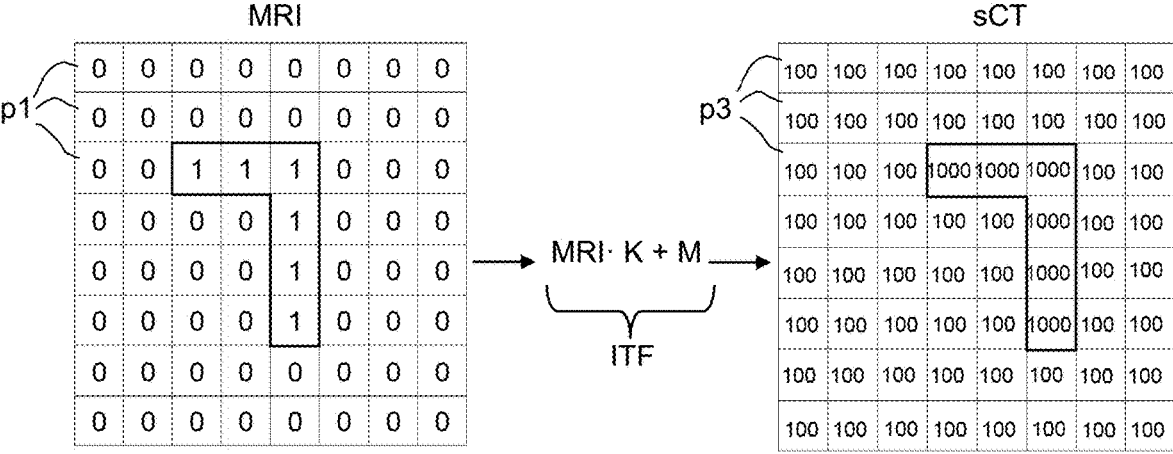

FIGS. 4A-4C will now be used for providing a qualitative and simplified explanation of some technical advantages of generating and using a parameterized ITF in accordance with the foregoing.

FIG. 4A is intended to represent the prior art technique of direct image-to-image mapping from an MR image into an sCT image by a trained neural network, e.g. as described in the Background section. The top of FIG. 4A illustrates matched MR and CT images, each comprising respective pixels p1, p2 with exemplifying signal values ("intensity values"). The MR and CT images both represent an inverted L structure, which yields pixel values of 1 against a background of pixel values of 0 in the MR image (top left) and pixel values of 1000 against a background of pixel values of 100 in the CT image (bottom left). A slight misalignment of one pixel is introduced between the MR and CT images in the horizontal direction. Assuming that the neural network is trained based on a large number of matched MR and CT images with a small misalignment, e.g. as represented by the three additional instances of matched MR and CT images in FIG. 4A, the trained neural network may produce the sCT image shown at the bottom of FIG. 4A based on the MR image shown at the top left. As seen from the signal values of the pixels p3 in the sCT image and indicated by thicker dashed lines, the inverted L structure is significantly blurred by the misalignment.

FIGS. 4B-4C illustrate an embodiment in which a machine-learning model has been trained to generate coefficients K, M of ITF=K·MRI+M, based on a large number of matched MR and CT images of the type shown in FIG. 4A, i.e. with a slight mutual misalignment. In FIG. 4B, an MR image representing an inverted L structure is input to the trained machine-learning model MLMT, which outputs [C] in the form of coefficient matrices or maps, namely a K matrix and an M matrix. The respective matrix comprises elements pK, pM that hold coefficient values ("pixel coefficients") and correspond to individual pixels p1 in the MR image. Thus, MLMT generates K, M coefficients for each pixel p1 in the incoming MR image. In FIG. 4C, the ITF is parameterized by the K and M matrices and operated on the same MR image that was input in FIG. 4B, resulting in the sCT image shown to the right. The pixel value of the respective pixel p3 in the sCT image is computed by operating the coefficient values of the corresponding elements pK, pM in the K and M matrices on the corresponding pixel value p1 in the MR image, in accordance with the ITF. As seen from the signal values of the pixels p3 in the sCT image and indicated by thicker lines, the inverted L structure is reproduced without blurring in the sCT image. Clearly, the generation of sCT images is robust to misalignment between images in the training set. In other words, the parameterized ITF enforces the propagation of details from the incoming MR image to the sCT image.

The example in FIGS. 4B-4C is simplified, in that MLMT is trained to generate [C] with the same coefficient values for all pixels in the incoming MR image. The present applicant has found that vastly improved results may be obtained by allowing the coefficient values to vary spatially within the image, i.e. between adjacent pixels in [C]. This means that in training, the machine-learning model MLM* is allowed to adapt coefficient values of the ITF to corresponding pixel values in the matched MR and CT images. In order to further stimulate that the ITF strives to propagate details from the MR image(s) to the sCT image(s) it may be advantageous to apply a constraint for the local variability of the coefficient values within the respective coefficient matrix. If MLM* is trained without such a restriction, the resulting MLMT might produce coefficient matrices with high variance, even to the extent that coefficient values between neighboring elements of the respective coefficient matrix are approximately independent. This is in contradiction to the physical environment where the MR images are taken and known properties of MR images. It is well-known that MR images may exhibit artifacts in the form of a slow-varying background component ("bias field") of image inhomogeneity and a non-standardness of the MR image intensity gray scale. In a non-limiting example, the slowly-varying bias field may have a spatial scale of about 10 cm between maximum and minimum values. The artifacts may thus cause the same tissue to yield different intensity values in different parts of an MR image. By applying the local variability constraint in training, it is ensured that MLMT generates [C] so that the respective coefficient values are slowly varying between matrix elements in the respective coefficient matrix, in approximate correspondence with the image inhomogeneity between pixels p1 in the incoming MR image caused by artifacts. The parameterized ITF may thereby at least partly compensate for the image inhomogeneity in the incoming MR image when generating the sCT image.

For example, the local variability constraint may be set such that the CV (coefficient of variation) of coefficient values in the respective coefficient matrix are significantly smaller than the CV of intensity values in a typical MR image, where the CV is determined in a local region of predefined extent around the respective element/pixel in the coefficient matrix/MR image. For example, the local region may include all pixels/elements within one pixel distance from the respective element/pixel, e.g. neighboring pixels in x, y, z directions.

The local variability constraint may be set to differ between coefficient matrices and may also differ within a coefficient matrix, i.e. the constraint may differ between matrix elements (pixel positions). Further, a local variability constraint need not be applied to all coefficient matrices.

Generally, the parameterized ITF may be seen as a regression function which has been adapted pixel for pixel between MR and CT images in the training set so as to yield individual pixel values of an sCT image based on corresponding pixel values in an incoming MR image.

The foregoing discussion demonstrates that embodiments of the invention are capable of reducing the impact of misalignment between MR and CT images in the training set and thereby achieving a high level of detail and accuracy in the resulting sCT images. Further, there is no need for preparatory segmentation of the images used for training MLM*, or of the MR images that are being input to MLMT, and thus both training and sCT generation may be fully automated without sacrificing accuracy. However, preparatory segmentation may be used, if desired.

A further technical advantage is that the sCT image may be generated with the same pixel resolution as the incoming MR image. In the prior art technique of using a neural network to perform a direct image-to-image mapping from an MR image to an sCT image, for the neural network to work efficiently, the neural network needs to be trained on MR and CT images that are resampled to a standardized pixel size. The standardized pixel size may be determined by the pixel size of the training set, or by hardware limitations, since a smaller standardized pixel size will require more computing resources which will limit the field-of-view and/or depth of the neural network. Thus, in the prior art technique, an incoming MR image may need to be resampled to the standardized pixel resolution before inference in the trained neural network, and the resulting sCT image is generated with the standardized pixel size. If the incoming MR image has smaller pixel size, i.e. more details, than the standardized pixel size, this additional level of detail will be irrevocably lost in the resampling process. In embodiments of the invention, the machine-learning model is dissociated from the resulting sCT image and instead generates the current [C]. This makes it possible to change the pixel size of the current [C], e.g. by interpolation, before the ITF is parametrized and applied to the incoming MR image, with no or only minor impact on the ability of the parameterized ITF to transfer details of the incoming MR image to the sCT image, especially if the parameterized ITF is a slowly varying function. In the above example of an affine ITF, the respective coefficient matrix K, M may be interpolated to increase the pixel resolution of the parameterized ITF, by adding one or more element values between existing elements in K, M. Any interpolation function may be used, including by not limited to a linear function. In the present disclosure, a process of increasing pixel size (and thus decreasing pixel resolution) is denoted "down-sampling", and a process of decreasing pixel size (and thus increasing pixel resolution) is denoted "up-sampling".

Figure 5:
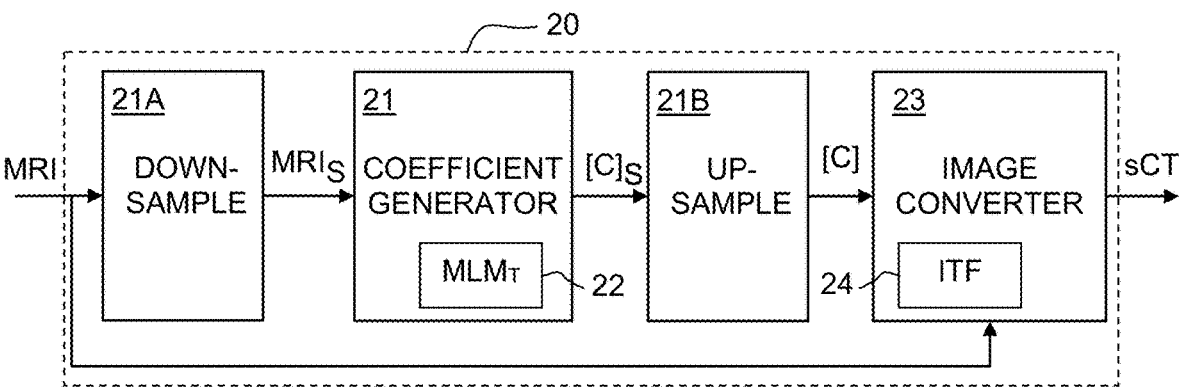
FIG. 5 is a block diagram of an imaging system in accordance with some embodiments of the present disclosure.

A corresponding embodiment is exemplified in FIG. 5, in which it is assumed that the pixel resolution of the incoming MR image, MRI, is higher than the predefined pixel resolution of the trained machine-learning model MLMT. A down-sampling device 21A is arranged upstream of the coefficient generator 21 to adapt the pixel resolution of the incoming MR image to the predefined pixel resolution. The coefficient generator 21 operates on the downsampled MR image to generate a set of coefficients of the predefined resolution. In FIG. 5, the downsampled MR image and the corresponding set of coefficients are designated by MRIS and [C]S, respectively. An up-sampling device 21B is arranged upstream of the image converter 23 to adapt the resolution of [C]S to the pixel resolution of the incoming MR image. The image converter 23 then operates on the up-sampled set of coefficients [C] to generate the sCT image with the same pixel resolution as the incoming MR image.

As understood from the foregoing, the set of coefficients generated by the coefficient generator 21 may be up-sampled or interpolated to any desired resolution before being input to the image converter 23, essentially without penalty on the level of detail in the resulting sCT image. Thus, MLMT may be configured to operate on a predefined or standardized pixel size that is significantly larger than the pixel size used in conventional direct image-to-image mapping by neural networks. The ability to train and operate the machine-learning model on larger pixels frees up computing resources. Thus, for given computing resources, embodiments of the invention enable deployment of machine-learning models with larger field-of-view and deeper layers, thereby increasing the performance of sCT image generation even further.

The technique exemplified in FIG. 5 may be similarly implemented in the training device 30 of FIG. 3B, e.g. by a down-sampling device being arranged upstream of the coefficient predictor 31, and an up-sampling device being arranged upstream of the image converter 33, which operates on the up-sampled [C]* to generate the sCT* image with the same pixel resolution as the incoming MR image.

It may be noted that it is equally possible to perform up-sampling of the incoming MR image, for example to match its resolution to the resolution of the MLMT, and to perform down-sampling of set of coefficients [C] to generate the sCT image with any desired resolution, for example the same pixel resolution as the incoming MR image. Generally, a first resampling may be performed on the incoming MR image and a second resampling may be performed on the set of coefficients, where the first and second resampling may differ, for example by changing the resolution in different directions.

Figure 6:
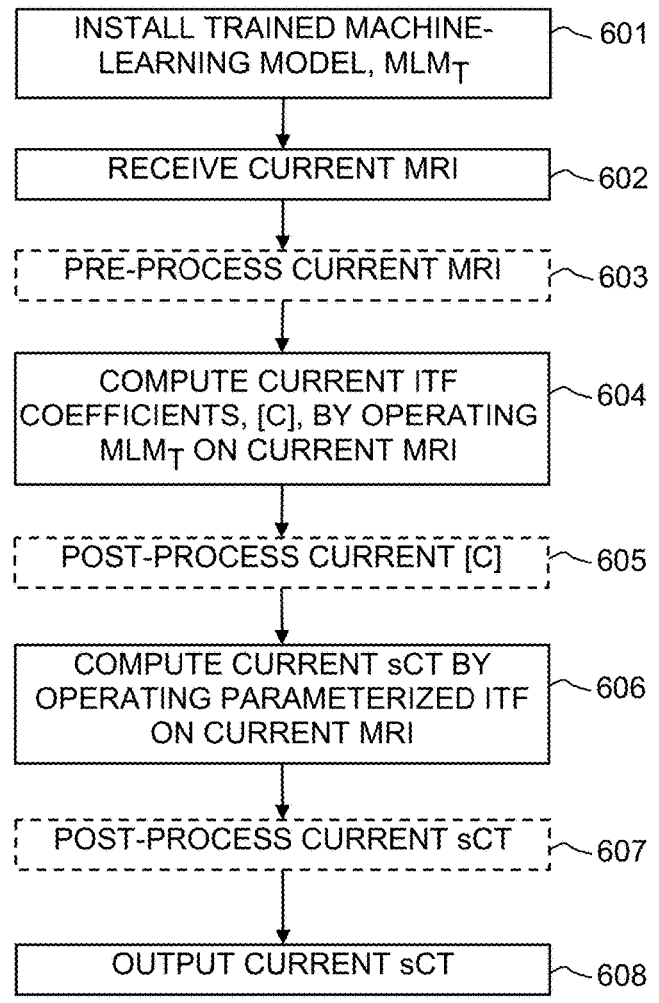
FIG. 6 is a flow chart of a method for generating an sCT image from an MR image in accordance with some embodiments of the present disclosure.

FIG. 6 illustrates an exemplifying method of generating an sCT image in accordance with an embodiment. The method may be implemented, e.g., by the conversion device 20 in FIG. 2 or FIG. 5. In step 601, a trained machine-learning model, MLMT, is received and installed, e.g. in computer memory. In step 602, a current MR image is received, e.g. from an MRI apparatus (cf. 10 in FIG. 2) or from a storage (cf. 100 in FIG. 2). The current MR image may be stored in computer memory. In an optional step 603, the current MR image may be pre-processed. Such pre-processing is known in the art and may involve a normalization with respect to any one of alignment, resolution, and intensity value distribution. Alternatively or additionally, step 603 may involve the above-mentioned re-sampling of the MR image to a predefined pixel resolution. Step 603 may also involve removing or masking certain portions in the MR image. Step 604 inputs the current MR image, optionally pre-processed, to the trained machine-learning model, MLMT, which thereby computes the set of coefficients [C] for the ITF. Thus, with reference to FIGS. 4B-4C, step 604 may populate the coefficient matrices K, M with current pixel coefficients at elements corresponding to pixels in the current MR image. The set of coefficients [C] may then be stored in computer memory.

In an optional step 605, the set of coefficients [C] are post-processed, e.g. by the above-mentioned up-sampling and/or by low-pass filtering. In step 606, the current sCT image is computed by applying the resulting set of coefficients [C], in accordance with the ITF (which is thereby parametrized), on the current MR image. In an optional step 607, the current sCT image may be post-processed, e.g. by removal or masking of certain portions, signal enhancement, noise removal, etc. In step 608, the current sCT image is output, e.g. for storage in a memory and/or for display, optionally together with the current MR image.

Figure 7:
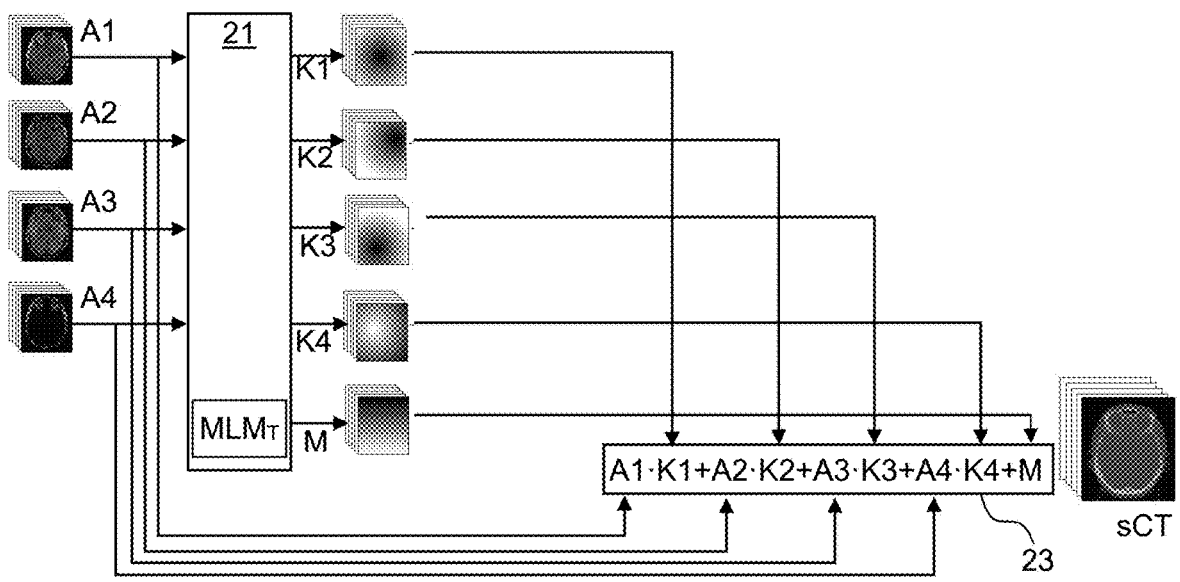
FIG. 7 is a functional block diagram of an implementation of the method in FIG. 6.

As already noted above, the current sCT may be computed based on two or more MR images, which may be generated for different settings of the MRI apparatus, e.g. different sequences or contrasts. As is known in the art, still further MR images may be generated by combining MR images, e.g. by computing the sum or difference between MR images. An illustrative example is given in FIG. 7, in which a coefficient generator 21 comprises machine-learning model MLMT that has been trained to compute a set of coefficients for four-channel MR images. In FIG. 7, the MR images of the different channels are designated A1-A4 and are illustrated as 3D images, i.e. a respective stack of 2D images. In one non-limiting example, A1 images may be acquired to emphasize fat, A2 images may be acquired to emphasize water, A3 images may be computed as A1+A2, and A4 may be computed as A1-A2. In the illustrated example, the coefficient generator 21 outputs one K matrix for each channel and one common M matrix for all channels. The K matrices of the different channels are designated K1-K4. Since the incoming MR images are 3D images, the resulting K and M matrices are also 3D matrices. As an alternative to a common M matrix, the coefficient generator 21 may be configured to output one M matrix for each channel. An image converter 23 then operates the K and M matrices on the images A1-A4 in accordance with an affine ITF to generate the sCT image, which is also a 3D image.

FIG. 7 is merely given as a non-limiting example. For the example of an affine ITF, the trained machine-learning model MLMT may be generally represented as a function that takes Nin incoming MR images to generate Nout coefficient matrices $K_1, \ldots, K_{Nout-1}$, $M \in \mathbb{R}^{Nx \times Ny \times Nz}$, but only has to apply the coefficient matrices to a subset of the MR images. This means that MLMT may represented as a function:

$$h(A_1, \ldots, A_{Nin}) = (K_1, \ldots, K_{Nout-1}, M) \tag{1}$$

For example, an affine ITF that operates on the coefficient matrices may be represented as:

$$\tilde{C} = f(A_1, \ldots, A_{Nin}) = M + \sum_{m=1}^{Nout-1} K_m \odot A_{g(m)} \tag{2}$$

where $\tilde{C}$ is the sCT image, g(m) is a mapping function that defines the mapping between coefficient matrix and MR image, and $\odot$ represents an element-wise multiplication. The skilled person is readily able to derive corresponding equations for non-linear ITFs.

Figure 8A:
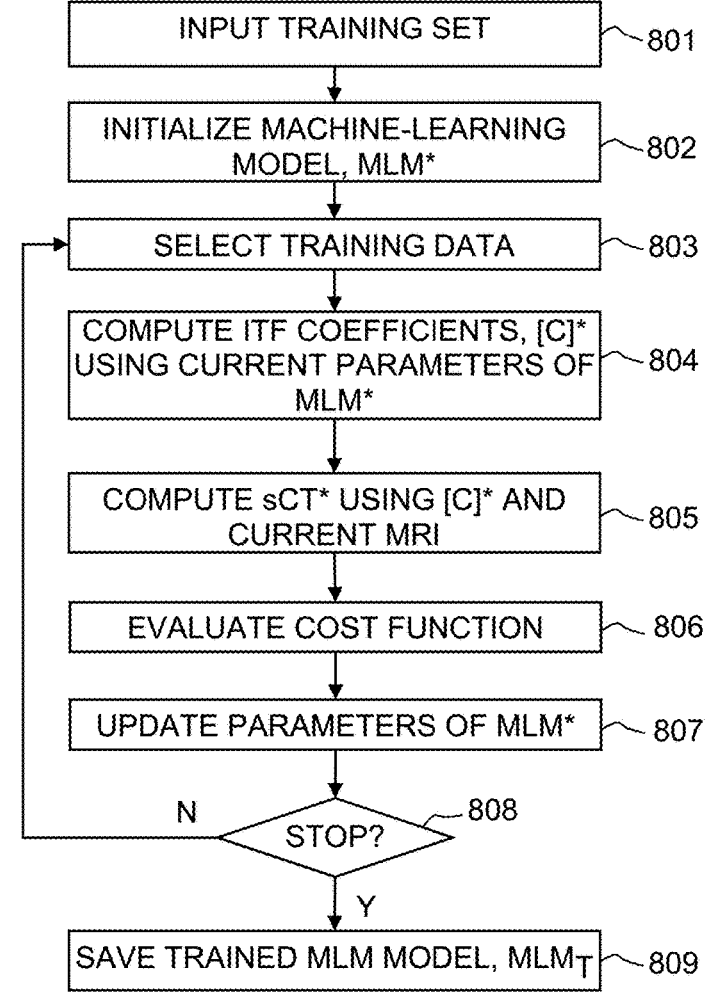
FIG. 8A is a flow chart of a method for training a machine-learning model for subsequent use in the method of FIG. 6, and FIGS. 8B-8C are functional block diagrams of implementations of the method in FIG. 8A.

FIG. 8A illustrates an exemplifying method of training a machine-learning model MLM* in accordance with an embodiment. The method may be implemented, e.g., by the training device 30 in FIGS. 3A-3B. As understood from the foregoing, the method is performed to learn model parameters of MLM* for a specific ITF, based on training images comprising single- or multi-channel MR images of an anatomical area of a patient, and corresponding CT images acquired by a CT scan of the same or similar anatomical area of the patient. The output of the method is a trained machine-learning model MLMT.

In step 801, a training set of matched MR and CT images (cf. 210 in FIG. 3C) is input and stored in memory (cf. 200 in FIG. 3A). In step 802, MLM* is initialized, which may involve initializing an iteration index, starting parameters of MLM*, etc. Steps 803-808 may be performed iteratively until one or more predefined stopping criteria are met (e.g., the iterative process converges according to a predefined criterion). In step 803, training images are selected from the training set, e.g., randomly, where the training images comprise matched MR and CT images. Step 803 may also involve pre-processing the training images. Step 804 computes a predicted set of coefficients [C]* according to the current model parameters of MLM* for the training images. Step 805 computes the sCT* image given by ITF when parameterized by [C]* and operated on the MR image(s) in the training images. Step 806 evaluates a cost function. For example, the cost function may determine a difference between the CT image in the training images and the sCT* image. Such a difference may, e.g., correspond to an error map indicating the differences in pixel values between the two images. The difference may be quantified by any known regression loss function, e.g. comprising calculation of mean absolute error (MAE), mean squared error (MSE), Huber loss, Log-cosh loss, etc. Step 807 determines or updates model parameters of the MLM* based on the evaluation in step 806, e.g. by optimizing (minimizing or maximizing) the cost function with respect to the model parameters of the MLM*. In the example of neural networks, the model parameters may include weight and offset values, as is well known in the art. Step 807 may use any conventional update algorithm, including but not limited to backpropagation, stochastic gradient descent (SGD), Adaptive Moment Estimation (Adam), BFGS, Rprop, etc.

Step 808 determines whether a stopping criterion has been satisfied. Various stopping criteria may be used, such as a predetermined maximum number of iterations or a predetermined image quality measure given, e.g., by the cost function or another measure of the difference between the sCT* and CT images. If step 808 determines that the stopping criterion is not satisfied, it may return to step 803. Otherwise, MLM* is considered trained, and the training method proceeds to step 809 which stores or outputs MLMT for subsequent use by the generation method in FIG. 6.

As noted above, it has been found beneficial to apply a variability constraint during training to suppress large pixel-by-pixel variations within the respective coefficient matrix generated by the trained machine-learning model MLMT. The constraint may be applied at different stages of the training. In one example, the constraint may be embedded in the MLM* and thus applied during step 804. In another example, the constraint is applied as a low-pass filtration of [C]* in step 804. In yet another example, the constraint is included in the cost function and thus applied in step 806. It is realized that the constraint may take many different forms. In one example, the constraint operates to limit the variability within a local region of predefined extent around the respective pixel/element in the respective coefficient matrix. The predefined extent may be determined by testing.

Since training is an autonomous process, it is desirable to mitigate undesirable outcomes, which is achieved by applying the constraint. Without the constraint, there is a risk that the MLM* is trained to suppress details from the MR images in the SCT images that are generated by applying the parameterized ITF.

In one non-limiting example, the constraint is implemented as a total-variation (TV) penalty in the cost function. The TV penalty may be computed for each coefficient matrix and in each dimension. In the example that the local region extends one pixel in each dimension of 3D matrix B, the TV penalty may be defined as:

$$
TV(B) = \gamma_x \cdot \frac{1}{Nx \cdot Ny \cdot Nz} \sum_{x=1}^{Nx-1} \sum_{y=1}^{Ny} \sum_{z=1}^{Nz} |B(x+1, y, z) - B(x, y, z)| + \tag{3}
$$

$$
\gamma_y \cdot \frac{1}{Nx \cdot Ny \cdot Nz} \sum_{x=1}^{Nx} \sum_{y=1}^{Ny-1} \sum_{z=1}^{Nz} |B(x, y+1, z) - B(x, y, z)| +
$$

$$
\gamma_z \cdot \frac{1}{Nx \cdot Ny \cdot Nz} \sum_{x=1}^{Nx} \sum_{y=1}^{Ny} \sum_{z=1}^{Nz-1} |B(x, y, z+1) - B(x, y, z)|
$$

where $\gamma_x$, $\gamma_y$ and $\gamma_z$ are predefined weight factors and Nx, Ny, Nz designate the number of elements in the respective dimension x, y, z. The weighting factors may be tuned to offset differences in resolution between the dimensions, but also be set to enforce different amount of smoothness to each dimension. It should be noted that the enforced smoothness only affects [C]* generated by MLM* and does not result in a smoothing of the sCT* image. On the contrary, a smoothness that is enforced on [C]* during training will cause the MLMT to propagate details from the MR images to the sCT images.

In one example, MLM* may be trained for the affine ITF defined in Eq. 2 by including a penalty term p in the cost function:

$$
p(K_1, \ldots, K_{Nout-1}, M) = \gamma_0 \cdot TV(M \odot W_0) + \sum_{m=1}^{Nout-1} \gamma_m \cdot TV(K_m \odot W_m) \tag{4}
$$

where the weight matrices $W_m$ and the coefficient weight values $\gamma_m$ (m=0, ..., Nout−1) are optional. The weight matrices $W_m$ may be predefined to weight specific areas of the images to further enhance or relax the smoothness penalty, and the coefficient weight values $\gamma_m$ may be predefined to adjust the relative effect of the respective coefficient matrix on the penalty.

In the example that the cost function comprises a computation of MAE for the error map, Eq. 2 and Eq. 4 may be combined into a cost function L:

$$
L(K_1, \ldots, K_{Nout-1}, M) = \tag{5}
$$

$$
\frac{1}{N} \cdot \left( \sum_{n=1}^{N} \left\| C_n - \tilde{C}_n(K_1, \ldots, K_{Nout-1}, M) \right\| + p(K_1, \ldots, K_{Nout-1}, M) \right)
$$

where $\|\cdot\|$ denotes a chosen norm.

An illustrative example of the training method of FIG. 8A is given in FIG. 8B, which depicts a training device that operates on single-channel 2D MR images and is configured in correspondence with FIG. 3B. A coefficient predictor 31 operates on the MR image to generate [C]* in the form of predicted K* and M* matrices (step 804). An image converter 33 operates the ITF, parameterized by K* and M*, on the MR image to generate a predicted sCT* image (step 805). The prediction evaluator 35 in FIG. 3B corresponds to a cost function calculator 35A and a model parameter updater 35B in FIG. 8B. The cost function calculator 35A computes the terms of the cost function, including the mean absolute error between the sCT* and CT images (MAE), the TV penalty of K* (TVK), and the TV penalty of M* (TVM), and combines MAE, TVK and TVM into a current value of the cost function (step 806). The model parameter updater 35B computes updated values of model parameters of MLM* to reduce the current value of cost function in subsequent iterations (step 807).

FIG. 8C illustrates an alternative embodiment of the training device 30. This embodiment presumes that a target set of coefficients has been pre-computed, e.g. by operating another machine-learning model (not shown) on a target set of matched MR and CT images, or by another type of computation or estimation process. The target set of coefficients is designated [C]TAR in FIG. 8C and may, e.g., comprise one or more target K matrices and a target M matrix. The target device 30 in FIG. 8C operates on a training set of MR images. In relation to the embodiment of

15

FIG. 3B, the target device 30 comprises an identical coefficient predictor 31, which computes a predicted set of coefficients [C]*, but lacks the image converter 33. Further, the prediction evaluator 35 is arranged to evaluate a cost function that compares [C]* to [C]TAR and to generate, based on the evaluated cost function, feedback data FB* that causes the coefficient predictor 31 to update the model parameters of MLM*. Compared to the method in FIG. 8A, the training device 30 in FIG. 8C performs a corresponding method in which step 805 is omitted and at least steps 806-807 are modified. The training device 30 in FIG. 8C may also apply the above-mentioned constraint, e.g. in the cost function.

Generally, any of the methods described herein, or part thereof, may be implemented in a processing device by a combination of software and hardware circuitry, or exclusively by tailored hardware circuitry. FIG. 9 is a block diagram of an exemplifying structure of such a processing device 90. In FIG. 9, the processing device 90 comprises a control circuit 91 responsible for the overall operation of the processing device 90. As shown, the control circuit 91 may include a processor 92, which may include a central processing unit (CPU), graphics processing unit (GPU), microcontroller, microprocessor, ASIC, FPGA, or any other specific or general processing device, or any combination thereof. The processor 92 may execute instructions 93 stored in a separate memory, such as memory 93, and/or in an internal memory (not shown) of the control circuit 91, in order to control the operation of the processing device 90. The instructions 94 when executed by the processor 92 may cause the processing device 80 to perform any of the methods described herein, or part thereof. As indicated in FIG. 9, the memory 93 may also store data 95 for use by the processor 92. Depending on implementation, the data 95 may comprise one or more of data items described above and/or depicted in the drawings, such as MLMT, MLM*, [MRI], [CT], [C]PRE, etc. The memory 93 may comprise one or more of a buffer, a flash memory, a hard drive, a removable media, a volatile memory, a non-volatile memory, a random access memory (RAM), or another suitable device. In an exemplary arrangement, the memory 93 includes a non-volatile memory for long term data storage and a volatile memory that functions as system memory for the control circuit 91. The memory 93 may exchange data with the control circuit 91 over a data bus. Accompanying control lines and an address bus between the memory 93 and the control circuit 91 also may be present. The memory 93 is considered a non-transitory computer readable medium.

As indicated in FIG. 9, the instructions 94 may be supplied to the processing device 90 on a computer-readable medium 90A, which may be a tangible (non-transitory) product (e.g. magnetic medium, optical disk, read-only memory, flash memory, etc.) or a propagating signal.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

Further, while operations are depicted in the drawings in a particular order, this should not be understood as requiring that such operations be performed in the particular order shown or in sequential order, or that all illustrated operations be performed, to achieve desirable results. In certain circumstances, parallel processing may be advantageous.

Further, all of the foregoing methods, devices, embodiments, examples and aspects are equally applicable for generating an sCT image based on an origin image acquired by a medical imaging apparatus using another imaging modality than MRI, e.g. Cone Beam Computed Tomography (CBCT), Positron Emission Tomography (PET), Single-Photon Emission Computed Tomography (SPECT), Magnetic Particle Imaging (MPI), etc. It is likewise conceivable to generate the sCT image based on two or more origin images, which may be acquired by at least two different imaging modalities. In one embodiment, a computer-implemented method for generating a synthetic electron density image of an anatomical portion may comprise: receiving a machine-learning model trained to predict coefficients of an image transfer function; receiving a current set of origin images of the anatomical portion; computing current coefficients of the image transfer function by operating the machine-learning model on the current set of origin images; and computing a current synthetic electron density image of the anatomical portion by operating the current coefficients, in accordance with the image transfer function, on the current set of origin images. At least one origin image in the set of origin images may be acquired by use of an imaging modality other than MRI, e.g. any one of CBCT, PET, SPECT and MPI.

In the following, a set of items are recited to summarize some aspects and embodiments of the invention as disclosed in the foregoing.

Item 1: A computer-implemented method for generating a synthetic electron density image (sCT) of an anatomical portion, said method comprising:

receiving (601) a machine-learning model (MLMT) trained to predict coefficients of an image transfer function;

receiving (602) a current set of magnetic resonance, MR, images of the anatomical portion;

computing (604) current coefficients ([C]) of the image transfer function by operating the machine-learning model (MLMT) on the current set of MR images; and computing (606) a current synthetic electron density image (sCT) of the anatomical portion by operating the current coefficients ([C]), in accordance with the image transfer function, on the current set of MR images.

Item 2: The computer-implemented method of item 1, wherein the machine-learning model (MLMT) is trained to predict the coefficients to achieve a similarity criterion between reference images (CT) and synthetic electron density images (sCT) generated by operating the coefficients, in accordance with the image transfer function, on MR images that correspond to the reference images (CT).

Item 3: The computer-implemented method of item 1 or 2, wherein the current coefficients ([C]) comprise one or more current pixel coefficients for a respective pixel location in the current set of MR images.

Item 4: The computer-implemented method of item 3, wherein the machine-learning model (MLMT) is trained to allow the one or more current pixel coefficients to vary between pixel locations.

Item 5: The computer-implemented method of item 3 or 4, wherein the one or more current pixel coefficients vary between pixel locations.

Item 6: The computer-implemented method of any one of items 3-5, wherein the machine-learning model (MLMT) is trained to allow the one or more pixel coefficients to vary between the pixel locations while adhering to a variability constraint of pixel coefficients within a predefined region around the respective pixel location.

Item 7: The computer-implemented method of any one of items 3-6, wherein said computing (606) the current synthetic electron density image (sCT) comprises operating the one or more current pixel coefficients, in accordance with the image transfer function, on one or more pixel values at the respective pixel location in the current set of MR images to generate a corresponding pixel value of the current synthetic electron density image (sCT).

Item 8: The computer-implemented method of any one of items 3-7, wherein said computing (604) the current coefficients ([C]) comprises populating one or more coefficient matrices (K, M) with current pixel coefficients at matrix elements corresponding to pixels in the respective MR image.

Item 9: The computer-implemented method of item 8, wherein said computing (606) the current synthetic electron density image (sCT) comprises operating the one or more coefficient matrices (K, M), in accordance with the image transfer function and element-wise, on pixel values in the current set of MR images.

Item 10: The computer-implemented method of claim 9, wherein said computing (604) the current coefficients ([C]) comprises a first resampling of the current set of MR images before operating the machine-learning model (MLMT) on the current set of MR images, wherein said method further comprises a second resampling of the one or more coefficient matrices (K, M) before operating the one or more coefficient matrices (K, M) in accordance with the image transfer function and element-wise, on the pixel values in the current set of MR images as received.

Item 11: The computer-implemented method of item 10, wherein the first resampling changes a resolution of the current set of MR images to a resolution expected by the trained machine-learning model (MLMT), and wherein the second resampling changes a resolution of the one or more coefficient matrices (K, M) to a target resolution equal to the resolution of the current set of MR images.

Item 12: The computer-implemented method of item 10 or 11, wherein the first resampling is a down-sampling and the second resampling is an up-sampling.

Item 13: The computer-implemented method of any preceding item, wherein the image transfer function is a polynomial function.

Item 14: The computer-implemented method of any preceding item, wherein the image transfer function is an affine function.

Item 15: The computer-implemented method of any preceding item, wherein the machine-learning model (MLMT) comprises an artificial neural network, ANN.

Item 16: A computer-readable medium comprising computer instructions (94) which, when executed by a processor (92), cause the processor (92) to perform the method of any one of items 1-15.

Item 17: A device for generating a synthetic electron density image (sCT) of an anatomical portion, said device comprising a processor (92) which is configured to:

receive a machine-learning model (MLMT) trained to predict coefficients ([C]) of an image transfer function;

receive a current set of magnetic resonance, MR, images of the anatomical portion;

generate current coefficients ([C]) of the image transfer function (ITF) by operating the machine-learning model (MLMT) on the current set of MR images; and generate a current synthetic electron density image (sCT) of the anatomical portion by operating the current coefficients ([C]), in accordance with the image transfer function, on the current set of MR images.

Item 18: A system comprising a magnetic resonance imaging apparatus (10) which is configured to generate current MR images of an anatomical portion, and a device in accordance with item 17 which is arranged to receive the current MR images.

Item 19: A machine-learning model which is trained to predict coefficients ([C]) of an image transfer function to achieve a similarity criterion between reference images (CT) and synthetic electron density images (sCT), which are generated by operating the coefficients ([C]), in accordance with the image transfer function, on MR images that correspond to the reference images (CT).

Item 20: The machine-learning model of item 19, wherein the coefficients ([C]) comprise one or more pixel coefficients for a respective pixel location in the MR images, and wherein the machine-learning model is trained to allow the one or more pixel coefficients to vary between pixel locations.

Item 21: The machine-learning model of item 20, which is further trained to allow the one or more pixel coefficients to vary between the pixel locations in the respective MR image while adhering to a variability constraint of pixel coefficients within a predefined region around the respective pixel location.

Item 22: A computer-implemented method of providing a trained machine-learning model (MLMT) to predict coefficients of an image transfer function for use in generating a synthetic electron density image (sCT) of an anatomical portion as a function of a set of magnetic resonance, MR, images of the anatomical portion, said method comprising the steps of:

(a) initializing the machine-learning model (MLM*);

(b) obtaining training data comprising one or more MR images and one or more reference images (CT);

(c) operating the machine-learning model (MLM*) on the one or more MR images to generate predicted coefficients ([C]*) of the image transfer function;

(d) operating the predicted coefficients ([C]*), in accordance with the image transfer function, on the one or more MR images to generate one or more predicted synthetic electron density images (sCT*);

(c) evaluating a predefined cost function at least based on the reference images (CT) and the one or more predicted synthetic electron density images (sCT*);

(f) determining model parameter values for the machine-learning model (MLM*); and (g) repeating steps (b)-(f) for the model parameter values until a predefined criterion is fulfilled; and (h) outputting the model parameter values for the machine-learning model (MLMT).

Item 23: A method of providing a trained machine-learning model (MLMT) to predict coefficients of an image transfer function for use in generating a synthetic electron density image (sCT) of an anatomical portion as a function of a set of magnetic resonance, MR, images of the anatomical portion, said method comprising the steps of:

(a) initializing the machine-learning model (MLM*);

(b) obtaining pre-computed target coefficients ([C]TAR) of the image transfer function;

(c) operating the machine-learning model (MLM*) on the one or more MR images to generate predicted coefficients ([C]*) of the image transfer function;

(d) evaluating a predefined cost function at least based on the predicted coefficients ([C]*) and the pre-computed target coefficients ([C]TAR);

(e) determining model parameter values for the machine-learning model (MLM*); and (f) repeating steps (b)-(e) for the model parameter values until a predefined criterion is fulfilled; and (g) outputting the model parameter values for the machine-learning model (MLMT).

Item 24: The computer-implemented method of item 22 or 23, wherein the predicted coefficients ([C]*) comprise one or more predicted pixel coefficients for a respective pixel location in the one or more MR images, said method further comprising allowing the machine-learning model (MLM*) to vary the one or more pixel coefficients between the pixel locations.

Item 25: The computer-implemented method of item 24, further comprising applying a variability constraint of pixel coefficients within a predefined region around the respective pixel location.

Item 26: The computer-implemented method of item 25, wherein the variability constraint is applied by the machine-learning model (MLM*) or by the predefined cost function, or by processing the predicted coefficients ([C]*).

Item 27: A computer-readable medium comprising computer instructions (94) which, when executed by a processor (92), cause the processor (92) to perform the computer-implemented method of any one of items 22-26.

What is claimed is:

1. A computer-implemented method for generating a synthetic electron density image of an anatomical portion from a current set of origin images, said method comprising:

receiving a machine-learning model trained to predict coefficients of an image transfer function from the current set of origin images, the image transfer function being a predefined parametric function containing the coefficients, receiving the current of origin images of the anatomical portion, wherein the current set of origin images is acquired by use of at least one imaging modality, computing current coefficients of the image transfer function by operating the machine-learning model on the current set of origin images, and following computing of the current coefficients of the image transfer function, computing the synthetic electron density image of the anatomical portion by operating the predefined parametric function of the image transfer function populated with the current coefficients on the current set of origin images on which the machine-learning model was operated to compute the current coefficients of the image transfer function.

2. The computer-implemented method of claim 1, wherein the machine-learning model is trained to predict the coefficients to achieve a similarity criterion between reference images and synthetic electron density images generated by operating the coefficients, in accordance with the image transfer function, on origin images that correspond to the reference images.

3. The computer-implemented method of claim 1, wherein the current coefficients comprise one or more current pixel coefficients for a respective pixel location in the current set of origin images.

4. The computer-implemented method of claim 3, wherein the machine-learning model is trained to allow the one or more current pixel coefficients to vary between pixel locations.

5. The computer-implemented method of claim 3, wherein the one or more current pixel coefficients vary between pixel locations.

6. The computer-implemented method of claim 3, wherein the machine-learning model is trained to allow the one or more pixel coefficients to vary between the pixel locations while adhering to a variability constraint of pixel coefficients within a predefined region around the respective pixel location.

7. The computer-implemented method of claim 3, wherein said computing the current synthetic electron density image comprises operating the one or more current pixel coefficients, in accordance with the image transfer function, on one or more pixel values at the respective pixel location in the current set of origin images to generate a corresponding pixel value of the current synthetic electron density image.

8. The computer-implemented method of claim 3, wherein said computing the current coefficients comprises populating one or more coefficient matrices with current pixel coefficients at matrix elements corresponding to pixels in the respective origin image.

9. The computer-implemented method of claim 8, wherein said computing the current synthetic electron density image comprises operating the one or more coefficient matrices, in accordance with the image transfer function and element-wise, on pixel values in the current set of origin images.

10. The computer-implemented method of claim 9, wherein said computing the current coefficients comprises a first resampling of the current set of origin images before operating the machine-learning model on the current set of origin images, wherein said method further comprises a second resampling of the one or more coefficient matrices before operating the one or more coefficient matrices in accordance with the image transfer function and element-wise, on the pixel values in the current set of origin images as received.

11. The computer-implemented method of claim 10, wherein the first resampling changes a resolution of the current set of origin images to a resolution expected by the trained machine-learning model, and wherein the second resampling changes a resolution of the one or more coefficient matrices to a target resolution equal to the resolution of the current set of origin images.

12. The computer-implemented method of claim 10, wherein the first resampling is a down-sampling and the second resampling is an up-sampling.

13. The computer-implemented method of claim 1, wherein the image transfer function is a polynomial function or an affine function.

14. The computer-implemented method of claim 1, wherein the machine-learning model comprises an artificial neural network, ANN.

15. A non-transitory computer-readable medium comprising computer instructions which, when executed by a processor, cause the processor to perform the method of claim 1.

16. A device for generating a synthetic electron density image of an anatomical portion from a current set of origin images, said device comprising a processor which is configured to:

receive a machine-learning model trained to predict coefficients of an image transfer function from the current set of origin images, the image transfer function being a predefined parametric function containing the coefficients;

receive the current set of origin images of the anatomical portion, said origin images representing a parameter other than electron density;

generate current coefficients of the image transfer function by operating the machine-learning model on the current set of origin images; and following generation of the current coefficients of the image transfer function, generate the synthetic electron density image of the anatomical portion by operating the predefined parametric function of the image transfer function populated with the current coefficients on the current set of origin images on which the machine-learning model was operated to generate the current coefficients of the image transfer function.

17. A system comprising a magnetic resonance imaging apparatus which is configured to generate current origin images of an anatomical portion, and a device in accordance with claim 16 which is arranged to receive the current origin images.

18. A non-transitory computer readable medium storing a machine-learning model, the machine-learning model trained to determine coefficient values of an image transfer function to achieve a similarity criterion between reference images and synthetic electron density images, the image transfer function being a predefined parametric function containing the coefficients which generates the synthetic electron density images by operating the predefined parametric function of the image transfer function populated with the determined coefficients on origin images that correspond to the reference images.

19. The non-transitory computer readable medium storing the machine-learning model of claim 18, wherein the coefficients comprise one or more pixel coefficients for a respective pixel location in the origin images, and wherein the machine-learning model is trained to allow the one or more pixel coefficients to vary between pixel locations.

20. The non-transitory computer readable medium storing the machine-learning model of claim 19, wherein the machine-learning model is further trained to allow the one or more pixel coefficients to vary between the pixel locations in the respective origin image while adhering to a variability constraint of pixel coefficients within a predefined region around the respective pixel location.

21. The computer-implemented method of claim 1, wherein said at least one imaging modality is selected from a group consisting of Cone Beam Computed Tomography (CBCT), Positron Emission Tomography (PET), Single-Photon Emission Computed Tomography (SPECT), Magnetic Particle Imaging (MPI), and Magnetic Resonance Imaging (MRI).

22. The computer-implemented method of claim 9, wherein said computing the current coefficients comprises a post-processing of the one or more coefficient matrices before operating the one or more coefficient matrices in accordance with the image transfer function and element-wise, on the pixel values in the current set of origin images as received.

23. The computer-implemented method of claim 22, wherein said post-processing comprises an up-sampling or a down-sampling of the one or more coefficient matrices.

* * * * *